(12) United States Patent
Saoji et al.

(10) Patent No.: US 8,768,476 B2
(45) Date of Patent: *Jul. 1, 2014

(54) METHODS AND SYSTEMS OF COMPENSATING FOR A DISABLED ELECTRODE

(75) Inventors: Aniket Saoji, Northridge, CA (US); Leonid M. Litvak, Los Angeles, CA (US)

(73) Assignee: Advanced Bionics, LLC, Valencia, CA (US)

(*) Notice: Subject to any disclaimer, the term of this patent is extended or adjusted under 35 U.S.C. 154(b) by 181 days.

This patent is subject to a terminal disclaimer.

(21) Appl. No.: 13/425,741

(22) Filed: Mar. 21, 2012

(65) Prior Publication Data

US 2012/0179223 A1 Jul. 12, 2012

Related U.S. Application Data

(63) Continuation of application No. 12/421,620, filed on Apr. 9, 2009, now Pat. No. 8,165,689.

(60) Provisional application No. 61/043,713, filed on Apr. 9, 2008.

(51) Int. Cl.
*A61N 1/00* (2006.01)
*A61N 1/05* (2006.01)

(52) U.S. Cl.
CPC .................... *A61N 1/0541* (2013.01)
USPC ........................................................ 607/57

(58) Field of Classification Search
CPC .......... A61B 5/12; A61B 5/121; A61B 5/123; A61B 5/125; A61B 5/126; A61B 5/128; H04R 25/00; H04R 29/00; A61N 1/0541; A61N 1/36032

USPC ...................................................... 607/55–57
See application file for complete search history.

(56) References Cited

U.S. PATENT DOCUMENTS

| | | | |
|---|---|---|---|
| 4,400,590 A | 8/1983 | Michelson | |
| 4,532,930 A | 8/1985 | Crosby et al. | |
| 4,592,359 A | 6/1986 | Galbraith | |
| 4,947,844 A | 8/1990 | McDermott | |
| 5,824,022 A | 10/1998 | Zilberman et al. | |
| 6,219,580 B1 | 4/2001 | Faltys et al. | |
| 6,272,382 B1 | 8/2001 | Faltys et al. | |
| 6,308,101 B1 | 10/2001 | Faltys et al. | |
| 7,043,303 B1* | 5/2006 | Overstreet | 607/57 |
| 7,515,966 B1 | 4/2009 | Litvak et al. | |
| 2004/0136556 A1* | 7/2004 | Litvak et al. | 381/316 |

OTHER PUBLICATIONS

Non-Final Office Action received in U.S. Appl. No. 12/421,620, dated Apr. 14, 2011.
Final Office Action received in U.S. Appl. No. 12/421,620, dated Oct. 31, 2011.

* cited by examiner

*Primary Examiner* — Christopher D Koharski
*Assistant Examiner* — Roland Dinga
(74) *Attorney, Agent, or Firm* — ALG Intellectual Property, LLC

(57) ABSTRACT

An exemplary method includes 1) identifying, by a cochlear implant system, an electrode included within an array of electrodes as being a disabled electrode, 2) selecting, by the cochlear implant system, at least two non-adjacent electrodes surrounding the disabled electrode, and 3) simultaneously applying, by the cochlear implant system, stimulation current to the at least two non-adjacent electrodes to compensate for a loss of stimulation resulting from the disabled electrode. Corresponding methods and systems are also disclosed.

18 Claims, 14 Drawing Sheets

1000

Maps                                Electrodes

1) 16 Electrode Baseline  ○○○○○○○○○○○○○○○○

2) 9 Electrode SPAN       ○X○X○X○X○X○X○X○○

3) 13 Electrode SPAN      ○○XXX○○○○○○○○○○○

4) 13 Electrode SPAN      ○○○○○○○○○○XXX○○

5) 13 Electrode GAP       ○○XXX○○○○○○○○○○○

6) 13 Electrode GAP       ○○○○○○○○○○○○XXX○○

Fig. 10

METHODS AND SYSTEMS OF COMPENSATING FOR A DISABLED ELECTRODE

RELATED APPLICATIONS

The present application is a continuation application of U.S. patent application Ser. No. 12/421,620, filed Apr. 9, 2009, which claims priority under 35 U.S.C. §119(e) to U.S. Provisional Patent Application No. 61/043,713, filed on Apr. 9, 2008. Both of these applications are incorporated herein by reference in their respective entireties.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems generally employ an array of electrodes that is inserted into the cochlear duct. One or more electrodes of the array selectively stimulate different auditory nerves at different places in the cochlea based on the pitch of a received sound signal. Within the cochlea, there are two main cues that convey "pitch" (frequency) information to the patient. These are (1) the place or location of stimulation along the length of a cochlear duct and (2) the temporal structure of the stimulating waveform. In the cochlea, sound frequencies are mapped to a "place" in the cochlea, generally from low to high sound frequencies mapped from the apical to basilar direction. The electrode array is fitted to the patient to arrive at a mapping scheme such that electrodes near the base of the cochlea are stimulated with high frequency signals, while electrodes near the apex are stimulated with low frequency signals.

A sound processing heuristic may include any method, process, and/or algorithm that translates signals detected by a microphone into a sequence of electric pulses that can be transmitted to the intra-cochlear electrodes. However, one or more electrodes within an electrode array may become disabled or otherwise malfunction. Disabled electrodes may result in decreased sound quality and/or distorted pitch and may even render a cochlear implant useless to a patient.

SUMMARY

An exemplary method of compensating for a disabled electrode within an array of electrodes includes selecting at least two non-adjacent electrodes surrounding the disabled electrode and simultaneously applying stimulation current to the at least two non-adjacent electrodes. The stimulation current is configured to generate a pitch associated with the disabled electrode.

Another exemplary method of compensating for a disabled electrode within an array of electrodes includes providing an array of electrodes, stimulating a stimulation site within a patient and associated with a disabled electrode included within the array of electrodes by applying stimulation current to at least two non-adjacent electrodes selected from the array of electrodes and surrounding the disabled electrode, and adjusting the stimulation current to compensate for a loss of stimulation resulting from the disabled electrode.

An exemplary system for compensating for a disabled electrode includes a plurality of electrodes and an implantable cochlear stimulator electrically coupled to the plurality of electrodes. The implantable cochlear stimulator is configured to simultaneously apply stimulation current to at least two non-adjacent electrodes surrounding a disabled electrode included within the plurality of electrodes. The stimulation current is configured to generate a pitch associated with the disabled electrode.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 10 shows a number of electrode maps according to principles described herein.

DETAILED DESCRIPTION

Figure 1:
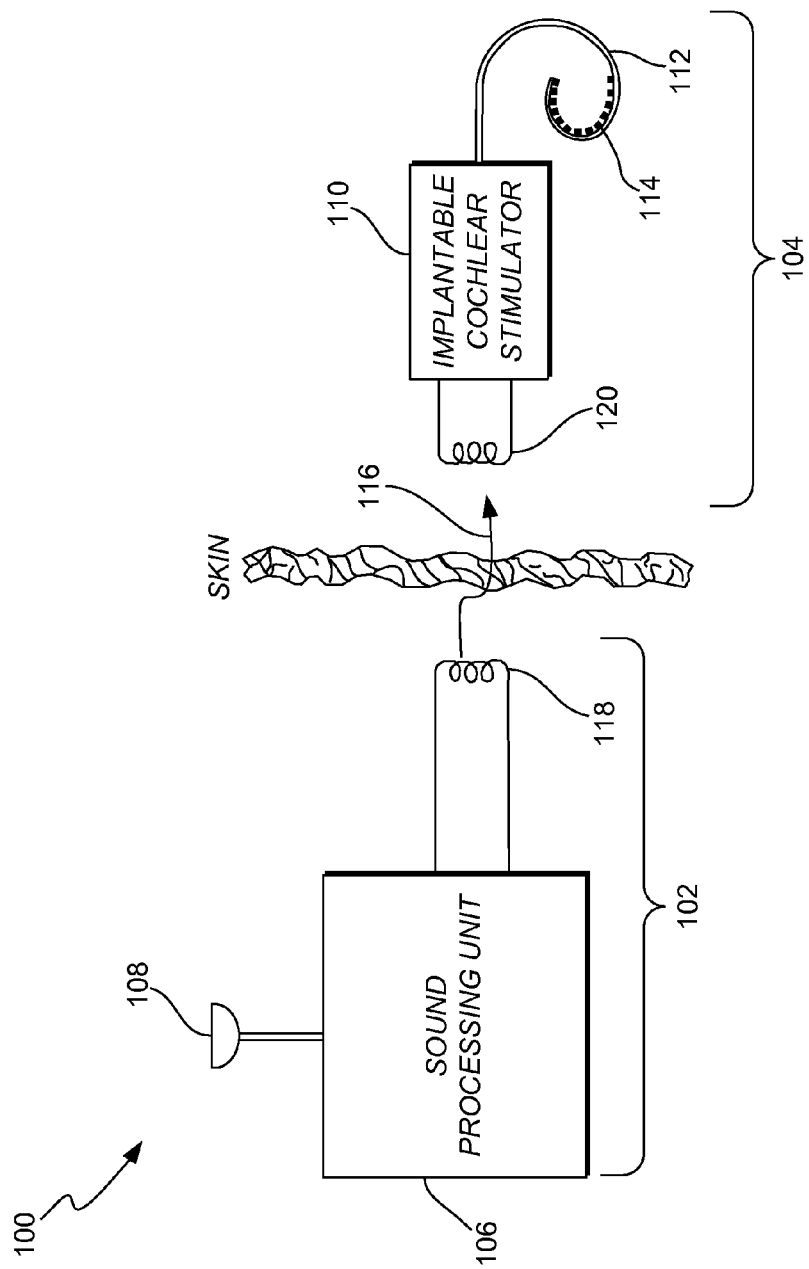
FIG. 1 illustrates an exemplary cochlear implant system according to principles described herein.

Methods and systems for compensating for a disabled electrode are described herein. As will be described in more detail below, the methods and systems may increase sound quality, provide pitches that a cochlear implant patient may not otherwise be able to experience, and improve an overall listening experience of the cochlear implant patient.

An exemplary method of compensating for a disabled electrode within an array of electrodes includes selecting at least two non-adjacent electrodes surrounding the disabled electrode and simultaneously applying stimulation current to the at least two non-adjacent electrodes. The stimulation current is configured to generate a pitch associated with the disabled electrode.

Another exemplary method of compensating for a disabled electrode within an array of electrodes includes providing an array of electrodes, stimulating a stimulation site within a patient and associated with a disabled electrode included within the array of electrodes by applying stimulation current to at least two non-adjacent electrodes selected from the array of electrodes and surrounding the disabled electrode, and adjusting the stimulation current to compensate for a loss of stimulation resulting from the disabled electrode.

An exemplary system for compensating for a disabled electrode includes a plurality of electrodes and an implantable cochlear stimulator electrically coupled to the plurality of electrodes. The implantable cochlear stimulator is configured to simultaneously apply stimulation current to at least two non-adjacent electrodes surrounding a disabled electrode included within the plurality of electrodes. The stimulation current is configured to generate a pitch associated with the disabled electrode.

As used herein, "simultaneously" applying stimulation current to two or more electrodes and variations thereof refer to concurrently applying the stimulation current to the two or more electrodes, and/or applying the stimulation current to the two or more electrodes at or about the same time. In many instances, simultaneous stimulation of electrodes is advantageous over sequential stimulation of electrodes because simultaneous stimulation requires less stimulation current to effectively generate a pitch associated with a disabled electrode surrounded by the electrodes.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

To facilitate an understanding of the methods and systems described herein, an exemplary cochlear implant system 100 will now be described in connection with FIG. 1. Exemplary cochlear implant systems suitable for use as described herein include, but are not limited to, those disclosed in U.S. Pat. Nos. 4,400,590; 4,532,930; 4,592,359; 4,947,844; 5,824,022; 6,219,580; 6,272,382; and 6,308,101. All of these listed patents are incorporated herein by reference in their respective entireties.

As shown in FIG. 1, the cochlear implant system 100, also referred to herein as a cochlear prosthesis, includes an external sound processor portion 102 and an implanted cochlear stimulation portion 104. The sound processor portion 102 may include a sound processing unit 106, a microphone 108, and/or additional circuitry as best serves a particular application. The cochlear stimulation portion 104 may include an implantable cochlear stimulator (ICS) 110, a lead 112 with an array of electrodes 114 disposed thereon, and/or additional circuitry as best serves a particular application. It will be recognized that the sound processor portion 102 may alternatively be located internal to the patient.

The microphone 108 of FIG. 1 is configured to sense acoustic signals and convert the sensed signals to corresponding electrical signals. The electrical signals are sent to the sound processing unit 106 over an electrical or other suitable link. Alternatively, the microphone 108 may be connected directly to, or integrated with, the sound processing unit 106.

The sound processing unit 106 may include any combination of hardware, software, and/or firmware as best serves a particular application. For example, the sound processing unit 106 may include one or more processors, digital signal processors (DSPs), filters, memory units, etc.

In some examples, the sound processing unit 106 may be configured to process the converted acoustic signals in accordance with a selected sound processing heuristic to generate appropriate control signals or stimulation parameters for controlling implantable cochlear stimulator 110. The electrical stimulation parameters may control various parameters of the stimulation current applied by implantable cochlear stimulator 110 to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, ramp on time, and ramp off time of the stimulation current that is applied to the stimulation site.

It will be recognized that the sound processing unit 106 shown in FIG. 1 is merely illustrative of the many different sound processing units that may be used in connection with the present systems and methods. For example, the sound processing unit 106 may include a behind-the-ear (BTE) unit configured to be positioned behind the ear. Alternatively, the sound processing unit 106 may include a portable speech processor (PSP) device, a conventional hearing aid, or any other type of sound processing unit. In certain examples, the sound processing unit 106 may be removed from behind the ear or other operating location by the patient prior to sleeping and replaced upon waking.

The lead 112 of FIG. 1 is adapted to be inserted within a duct of a patient's cochlea. As shown in FIG. 1, the lead 112 includes an array of electrodes 114 disposed along its length. It will be recognized that any number of electrodes 114 may be disposed along the lead 112 as may serve a particular application. Each of the electrodes 114 is electrically coupled to the implantable cochlear stimulator 110. Electronic circuitry within the implantable cochlear stimulator 110 may be configured to apply stimulation current to one or more selected electrodes 114 in accordance with a specified stimulation pattern controlled by the sound processing unit 106.

As mentioned, the implantable cochlear stimulator 110 and lead 112 may be implanted within the patient while the sound processing unit 106 and the microphone 108 are configured to be located outside the patient, e.g., behind the ear. Hence, the implantable cochlear stimulator 110 and the sound processing unit 106 may be transcutaneously coupled via a suitable data or communications link 116. The communications link 116 allows power and control signals to be sent from the sound processing unit 106 to the implantable cochlear stimulator 110. In some embodiments, data and status signals may also be sent from the implantable cochlear stimulator 110 to the sound processing unit 106.

The external and implantable portions of the cochlear implant system 100 may each include one or more coils configured to transmit and receive power and/or control signals via the data link 116. For example, the external portion 102 of the cochlear implant system 100 may include an external coil 118 and the implantable portion of the cochlear implant system 104 may include an implantable coil 120. The external coil 118 and the implantable coil 120 may be inductively coupled to each other, thereby allowing data and power signals to be wirelessly transmitted between the external portion and the implantable portion of the cochlear implant system 100. Because in certain embodiments, the external portion 102 of the cochlear implant system 100 may not always be within close proximity to the implantable portion of the cochlear implant system 104, such as when the external portion 102 is removed for sleeping, the system may be configured to recognize when the implantable coil 120 and the external coil 118 are within range of one another.

Figure 2:
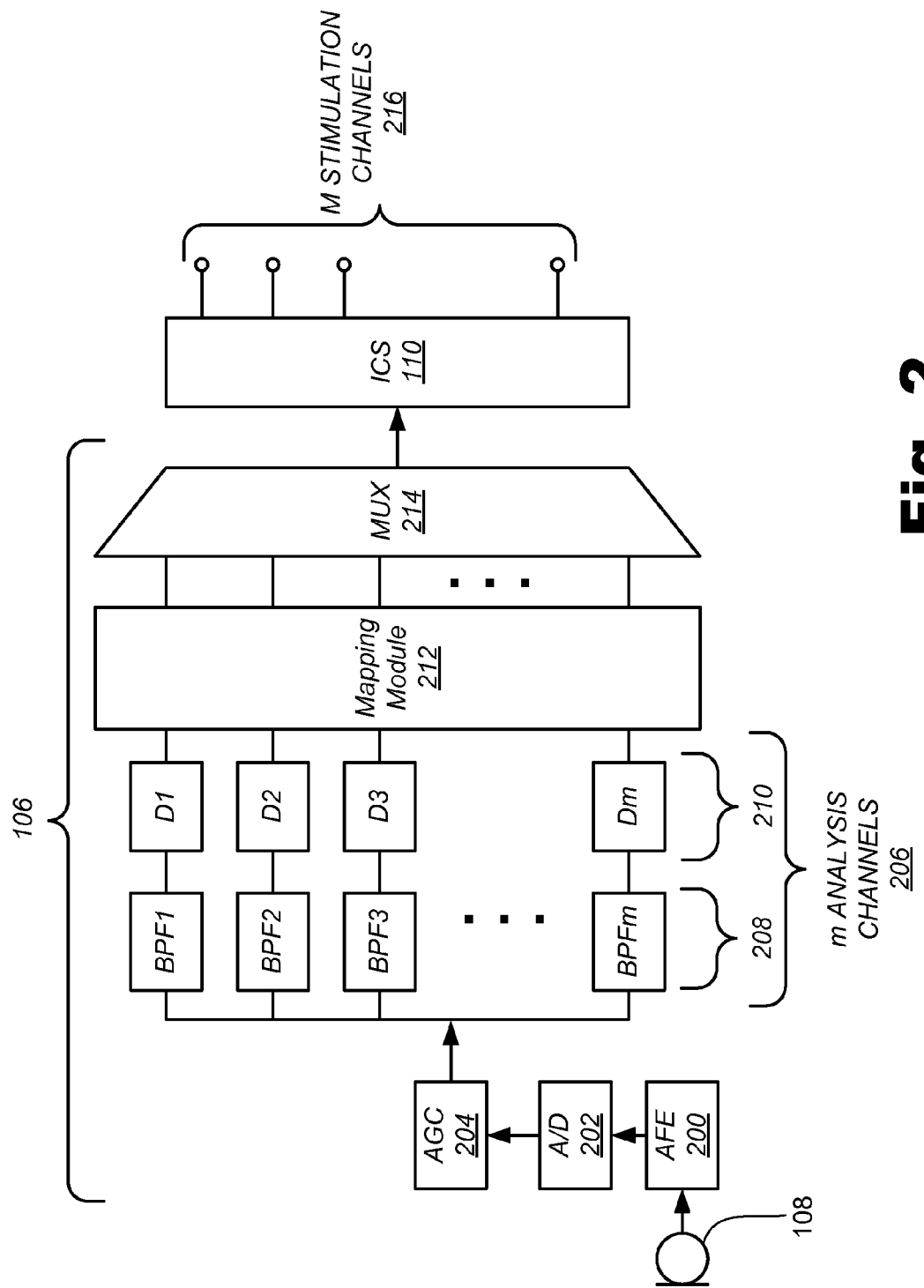
FIG. 2 is a functional block diagram of an exemplary sound processing unit and implantable cochlear stimulator according to principles described herein.

FIG. 2 is a functional block diagram of an exemplary sound processing unit 106 and implantable cochlear stimulator 110. The components shown in FIG. 2 are merely representative of the many different components that may be included within the sound processing unit 106 and/or the implantable cochlear stimulator 110. Each component may be implemented using any combination of hardware, software, and/or firmware. Although certain components are shown to be included within sound processing unit 106, it will be recognized that one or more of the components may alternatively be included within implantable cochlear stimulator 110. A more complete description of the functional block diagram of the sound processing unit 106 and the implantable cochlear stimulator 110 is found in U.S. Pat. No. 7,219,580, which is incorporated herein by reference in its entirety.

As shown in FIG. 2, the microphone 108 senses acoustic information, such as speech and music, and converts the acoustic information into one or more electrical signals. These signals are then amplified in audio front-end (AFE) circuitry 200. The amplified audio signal is then converted to a digital signal by an analog-to-digital (A/D) converter 202. The resulting digital signal is then subjected to automatic gain control using a suitable automatic gain control (AGC) function 204.

After appropriate automatic gain control, the digital signal is then processed in one of a number of digital signal processing or analysis channels 206. For example, the sound processing unit 106 may include, but is not limited to, eight analysis channels 206. Each analysis channel 206 may respond to a different frequency content of the sensed acoustical signal. In other words, each analysis channel 206 includes a band-pass filter (BP1-BPFm) 208 or other type of filter such that the digital signal is divided into m analysis channels 206. The lowest frequency filter may be a low-pass filter, and the highest frequency filter may be a high-pass filter.

As shown in FIG. 2, each of the m analysis channels 206 may also include an energy detection stage (D1-Dm) 210. Each energy detection stage 210 may include any combination of hardware, software, and/or firmware configured to detect the amount of energy contained within each of the m analysis channels (206). For example, each energy detection stage 210 may include a rectification circuit followed by an integrator circuit. In some examples, the cochlear implant system 100 may be configured to determine which of the m analysis channels 206 are presented to the patient via the stimulation channels 216 by analyzing the amount of energy contained in each of the m analysis channels 206.

After energy detection, the signals within each of the m analysis channels 206 are forwarded to a mapping module 212. The mapping module 212 is configured to map the signals in each of the m analysis channels 206 to one or more of M stimulation channels 216. In other words, the information contained in the m analysis channels 206 is used to define the stimulation current pulses that are applied to the patient by the implantable cochlear stimulator 110 via the M stimulation channels 216. In some examples, pairs or groups of individual electrodes 114 make up the M stimulation channels 216. Additionally or alternatively, one or more individual electrodes 114 may each represent one of the M stimulation channels 216.

In some examples, the mapped signals are serialized by a multiplexer 214 and transmitted to the implantable cochlear stimulator 110. The implantable cochlear stimulator 110 may then apply stimulation current via one or more of the M stimulation channels 216 to one or more stimulation sites within the patient's cochlea. As used herein and in the appended claims, the term "stimulation site" will be used to refer to a target area or location at which the stimulation current is applied. For example, a stimulation site may refer to any location within a region of auditory nerve tissue shown in FIG. 3. Through appropriate weighting and sharing of currents between electrodes 114, stimulation current may be applied to any stimulation site along the length of the lead 112.

Figure 3:
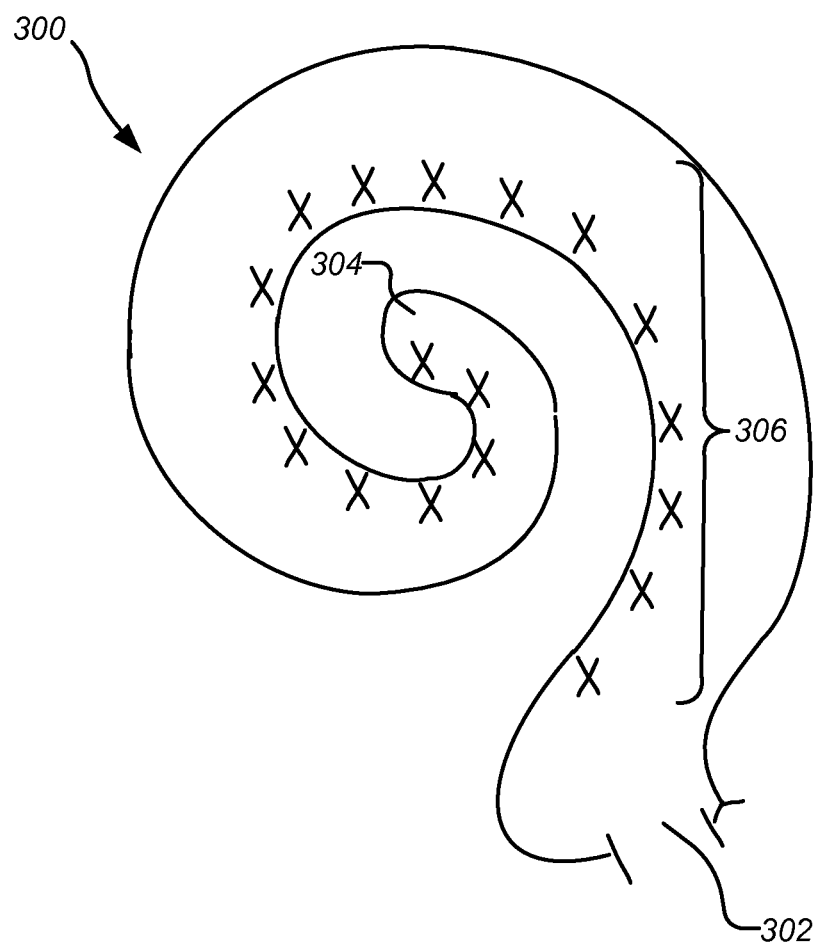
FIG. 3 illustrates a schematic structure of the human cochlea according to principles described herein.

FIG. 3 illustrates a schematic structure of the human cochlea 300. As shown in FIG. 3, the cochlea 300 is in the shape of a spiral beginning at a base 302 and ending at an apex 304. Within the cochlea 300 resides auditory nerve tissue 306, which is denoted by Xs in FIG. 3. The auditory nerve tissue 306 is organized within the cochlea 300 in a tonotopic manner. Low frequencies are encoded at the apex 304 of the cochlea 300 while high frequencies are encoded at the base 302. Hence, each location along the length of the cochlea 300 corresponds to a different perceived frequency or pitch. A cochlear prosthesis, such as cochlear implant system 100, may therefore be implanted within a patient with sensorineural hearing loss and configured to apply electrical stimulation to different locations within the cochlea 300 to provide the sensation of hearing. The terms "perceived frequency" and "pitch" will be interchangeably used herein to refer to a frequency of a sound as perceived by a cochlear implant patient.

Figure 4:
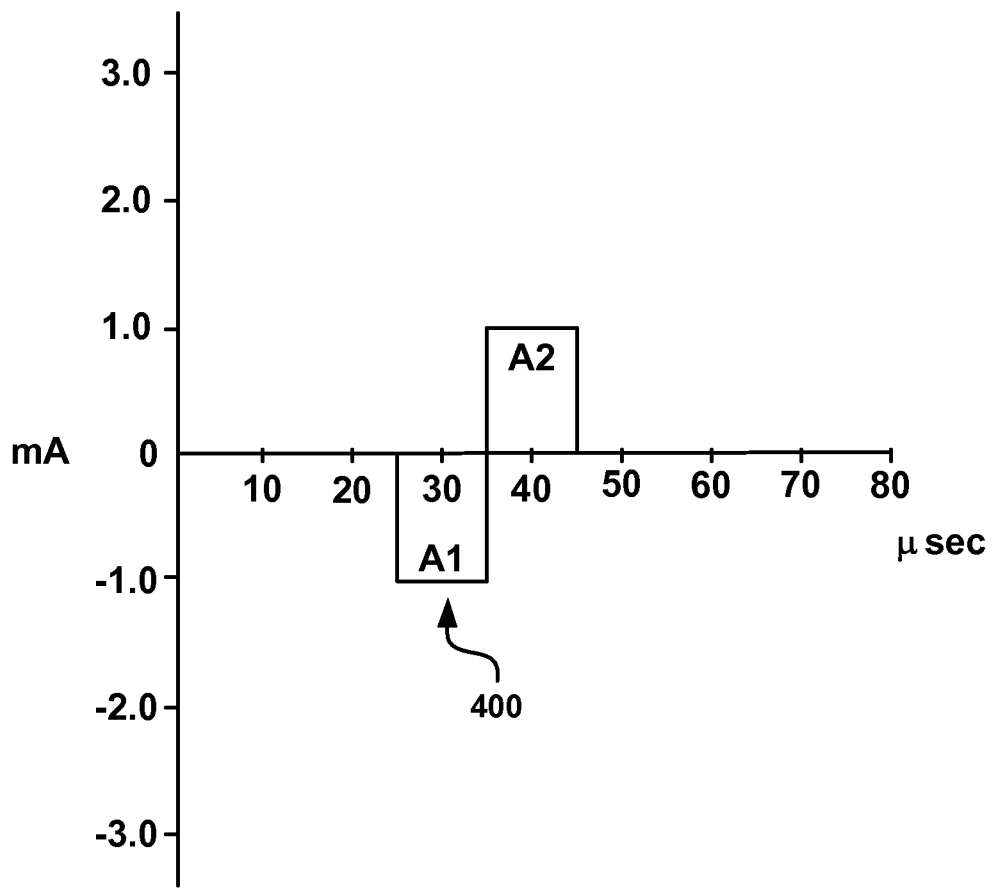
FIG. 4 illustrates an exemplary stimulation current pulse that may be delivered to neural tissue via one or more of stimulation channels according to principles described herein.

FIG. 4 illustrates an exemplary stimulation current pulse 400 that may be delivered to neural tissue via one or more of the stimulation channels 216. The stimulation current pulse 400 of FIG. 4 is biphasic. In other words, the pulse 400 includes two parts—a negative first phase having an area A1 and a positive second phase having an area A2. In some implementations, the negative phase A1 causes neural tissue to depolarize or fire. The biphasic stimulation pulse 400 shown in FIG. 4 has an amplitude of 1 milliamp (mA) and a pulse width of 20 microseconds (μsec) for illustrative purposes only.

The combined areas of A1 and A2 are representative of a total amount of electric charge that is applied to a stimulation site by stimulation current pulse 400. The biphasic stimulation pulse 400 shown in FIG. 4 is "charge balanced" because the negative area A1 is equal to the positive area A2. A charge-balanced biphasic pulse is often employed as the stimulus to minimize electrode corrosion and charge build-up which can harm surrounding tissue. However, it will be recognized that the biphasic stimulation pulse 400 may alternatively be charge-imbalanced as best serves a particular application.

In some examples, the systems and methods described herein may be used in connection with a current steering heuristic. Current steering may be used in configurations wherein a desired stimulation site is located spatially in between two electrodes. To effectively deliver stimulation to the stimulation site, weighted current may be applied simultaneously to two or more electrodes by implantable cochlear stimulator 110. The basis for current steering is the phenomenon of summation of electrical fields, where the current delivered to the two electrodes sums together. A stimulation site located spatially in between two electrodes may be effectively stimulated due to the summation of electrical fields.

Figure 5:
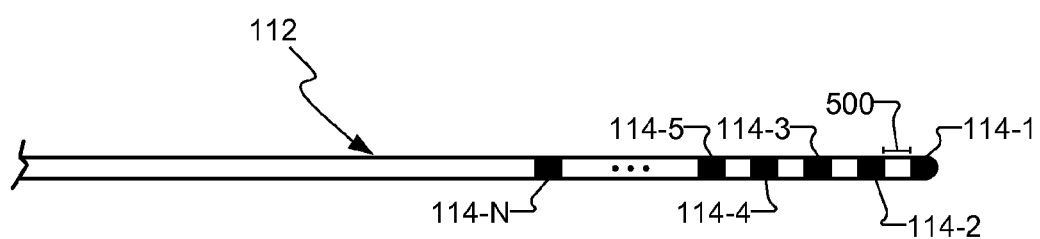
FIG. 5 shows an exemplary representation of a lead with a plurality of electrodes disposed thereon according to principles described herein.

To facilitate an understanding of the current steering heuristics described herein, FIG. 5 shows an exemplary representation of lead 112 with an array of electrodes 114-1 through 114-N (collectively referred to herein as "electrodes 114") disposed thereon. As used herein, two electrodes 114 may be "adjacent" one to another if they are located next to each other without any other electrodes 114 disposed therebetween. For example, electrodes 114-1 and 114-2 are adjacent one to another. "Non-adjacent" electrodes 114 have at least one other electrode 114 disposed therebetween along lead 112. For example, electrodes 114-1 and 114-3 are non-adjacent one to another because electrode 114-2 is disposed in between them.

Two or more electrodes (e.g., electrodes 114-1 and 114-2) may form a single channel through which electrical stimulation is applied to one or more stimulation sites. Alternatively, each electrode (e.g., electrode 114-1) may be associated with a distinct channel.

In some examples, a separation distance (e.g., distance 500) separates each adjacent electrode 114 along lead 112. The separation distance may be equal to any suitable value (e.g., substantially equal to 1 millimeter (mm)). In some examples, the separation distance between some electrodes 114 is different than the separation distance between other electrodes 114. A separation distance may also refer to a distance between non-adjacent electrodes (e.g., the distance between electrode 114-1 and 114-3).

Figure 6:
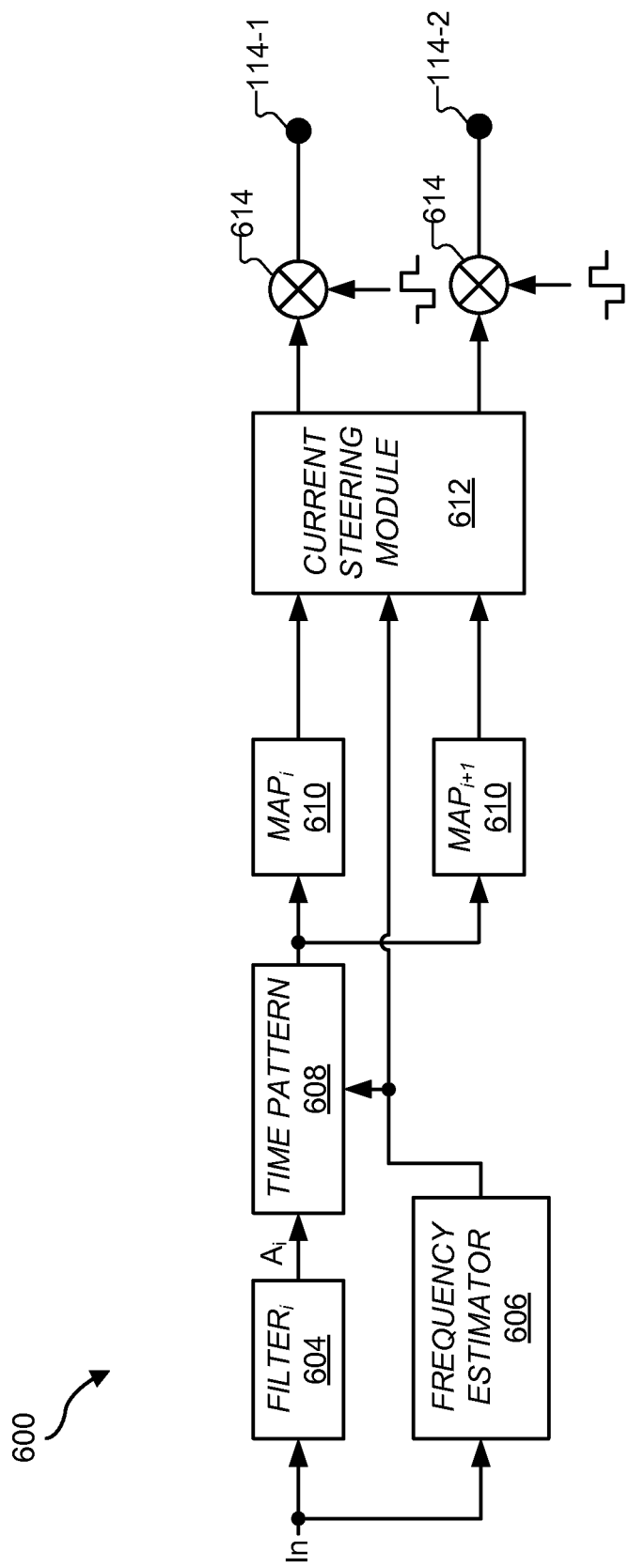
FIG. 6 is a functional block diagram of current steering components according to principles described herein.

Current steering may be used to stimulate a stimulation site located somewhere in between areas associated with two or more of the electrodes 114 shown in FIG. 5. To illustrate, FIG. 6 is a functional block diagram 600 of exemplary components that may be included within and/or implemented by sound processing unit 106, implantable cochlear stimulator 110, and/or any other component of cochlear implant system 100 to perform current steering in accordance with a current steering heuristic. The current steering may be applied to any two electrodes (e.g., electrodes 114-2 and 114-3). While FIG. 6 will be described in connection with electrodes 114-2 and 114-3, which are adjacent one to another, it will be recognized that the current steering heuristic may alternatively be applied to two or more non-adjacent electrodes (e.g., electrodes 114-1 and 114-3).

As shown in FIG. 6, an input signal is filtered by at least one filter 604 configured to divide the signal into a number of frequency channels or bands. The input signal is also input into a frequency estimator 606 configured to estimate the peak frequency thereof. A time pattern block 608 is configured to build construct the temporal structure of a pulse train representing the signal output by the at least one filter 604. Mapping modules 610 are configured to map the amplitude of the signal output by the time pattern block 608 to corresponding current levels in accordance with a suitable mapping function.

The output of each mapping module 610 is input into a current steering module 612. The current steering module 612 is also configured to receive the output of the frequency estimator 606. In some examples, the current steering module 612 is configured to determine appropriate weighting factors for current to be applied to electrodes 114-2 and 114-3. This determination may be based at least in part on the peak frequency estimate and the output of each of the mapping modules 610. The weighting factors may be applied to the current using multiplication blocks 614. In this manner, stimulation current may be delivered to a stimulation site located in between areas associated with electrodes 114-2 and 114-3.

Figure 7:
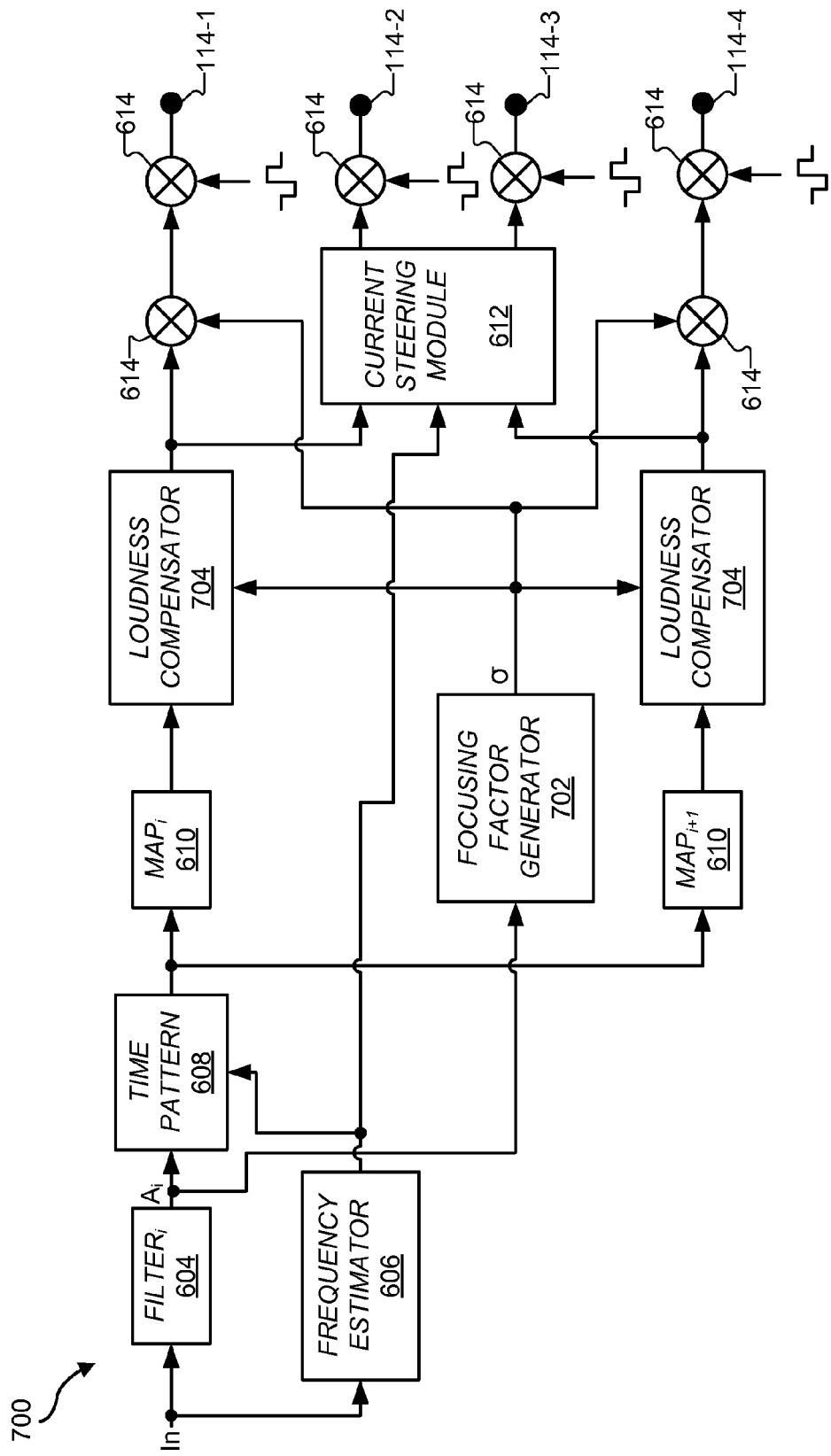
FIG. 7 is a functional block diagram of components configured to dynamically focus one or more excitation fields produced by current steering electrodes according to principles described herein.

The excitation field produced by the current steering electrodes 114-2 and 114-3 may be narrowed by applying compensating current simultaneously via one or more additional electrodes. FIG. 7 is a functional block diagram 700 of exemplary components that may be included within and/or implemented by sound processing unit 106, implantable cochlear stimulator 110, and/or any other component of cochlear implant system 100 to dynamically focus one or more excitation fields produced by current steering electrodes (e.g., electrodes 114-2 and 114-3). It will be recognized that the components shown in FIG. 7 are merely exemplary and that they may include additional or alternative components and/or functions as may serve a particular application.

The functional block diagram 700 described in connection with FIG. 7 includes many of the same components as the system of FIG. 6. In addition, functional block diagram 700 includes a focusing factor generator 702 configured to generate the aforementioned focusing factor σ based on the amplitude of the signal output by the filter 604. The focusing factor σ is used to generate scaled versions of the current steering current. This scaled current is delivered via one or more additional electrodes (e.g., electrodes 114-1 and 114-4) to effectively narrow the excitation field produced by electrodes 114-2 and 114-3.

As shown in FIG. 7, loudness compensators 704 may also be included within the system of FIG. 7. The loudness compensators 704 are configured to adjust the amplitudes of the currents applied via electrodes 114-2 and 114-3 to compensate for loudness changes that may be caused by current delivered via the compensating electrodes 114-1 and 114-4.

The current steering methods and systems described herein facilitate stimulation of stimulation sites located in between areas associated with physical electrodes 114. In other words, current steering facilitates "virtual electrodes" corresponding to each stimulation site located in between areas associated with physical electrodes 114.

As mentioned, one or more electrodes 114 within an electrode array may become disabled or otherwise malfunction. Disabled electrodes may result in decreased sound quality and/or distorted pitch and may even render a cochlear implant useless to a patient. In some examples, one or more disabled electrodes may be caused by a dead region within the cochlea of a particular patient. In this case, the patient may be unable to process complex stimulation patterns applied by the electrodes 114 to the dead region of the cochlea. However, the patient may still be able to process complex stimulation patterns applied to other regions of the cochlea that are functioning properly.

To this end, the present systems and methods provide for current steering between two or more electrodes 114 that are non-adjacent to one another, thus compensating for the loss of stimulation resulting from one or more disabled electrodes.

For example, cochlear implant system 110 may be configured to simultaneously apply stimulation current to at least two non-adjacent electrodes surrounding a disabled electrode in order to generate a pitch associated with the disabled electrode. Simultaneous stimulation of non-adjacent electrodes may be used to generate "virtual electrodes" that result in pitches that are substantially similar to those generated by the intermediate physical electrodes. As used herein, "stimulation of an electrode" and variations thereof will refer to delivering current to or through the electrode.

In some examples, sound processing unit 106 and/or cochlear implant system 110 may be configured to select which of the non-adjacent electrodes to stimulate in order to generate a pitch associated with a disabled electrode. The selection may be based on any of a number of factors, including, but not limited to, a separation distance between the non-adjacent electrodes, a proximity of the non-adjacent electrodes to the disabled electrode, and/or any other factor. For example, sound processing unit 106 and/or cochlear implant system 110 may select non-adjacent electrodes that are within a predetermined distance (e.g., 4 mm or any other distance) of each other.

A number of equal loudness contours will now be presented to show how the separation distance that separates non-adjacent electrodes one from another affects the ability of stimulation current applied to the non-adjacent electrodes to generate a pitch associated with a disabled electrode disposed between the non-adjacent electrodes. As will be described in more detail below, an equal loudness contour is configured to show an amount of current required to produce a most comfortable loudness sensation for a particular cochlear implant patient when applied to various combinations of electrodes 114.

Figure 8A:
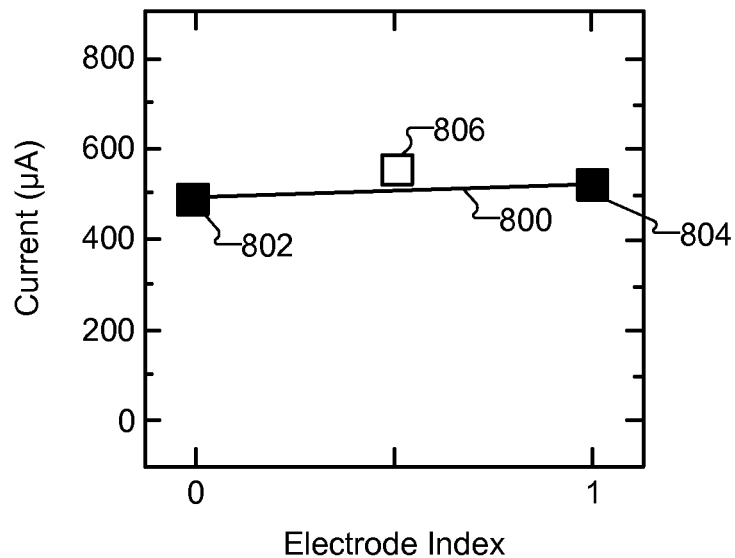
FIGS. 8A-8B show equal loudness contours corresponding to two adjacent electrodes according to principles described herein.
Figure 8B:
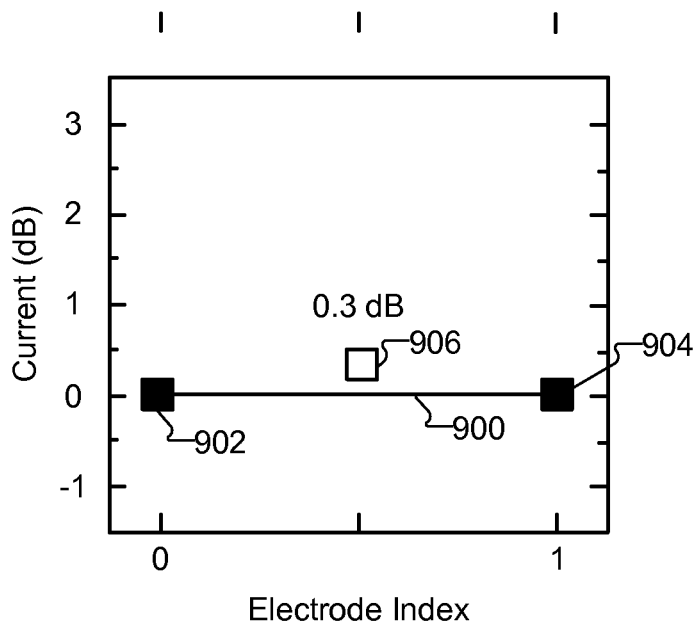

FIG. 8A shows an equal loudness contour 800 corresponding to two electrodes (e.g., electrodes 114-1 and 114-2) that are adjacent one to another along lead 112. FIG. 8B shows the same equal loudness contour 800 measured in accordance with a decibel (dB) scale for ease of comparison with other equal loudness contours. To generate equal loudness contour 800, an amount or level of stimulation current applied to the first electrode 114-1 that produces a particular loudness level as perceived by a particular cochlear implant patient is measured. The loudness level may correspond to a most comfortable loudness level or sensation for the patient. The resultant current level is represented by data point 802 and corresponds to an electrode index of 0 in FIGS. 8A-8B.

Stimulation current may then be applied to the second electrode 114-2 and adjusted until the same loudness level is perceived by the patient. For example, the stimulation current may be adjusted until it produces a most comfortable loudness sensation for the patient. The resultant current level is represented by data point 804 and corresponds to an electrode index of 1 in FIGS. 8A-8B. The equal loudness contour 800 may be represented by a line connecting data points 802 and 804.

Current steering may then be performed by simultaneously applying stimulation current to both electrodes 114-1 and 114-2. The loudness of the dual electrode stimulation is balanced to that of the individual electrodes 114-1 and 114-2. In other words, the stimulation current that is simultaneously applied to both electrodes 114-1 and 114-2 is adjusted until the same loudness level associated with each individual electrode 114-1 and 114-2 is achieved. The current level that results in a balanced loudness is represented by data point 806 and corresponds to an electrode index of 0.5.

In some examples, if there is summation of the electrical fields between two electrodes 114, the current level represented by data point 806 may be relatively close to the equal loudness contour 800. The distance between the current level represented by data point 806 and the equal loudness contour 800 will be referred to herein as an "elevation". The amount of elevation is inversely proportional to the degree of electrical field summation. For example, the current level 806 corresponding to simultaneous dual electrode stimulation shown in FIGS. 8A-8B has a relatively low amount of elevation (e.g., 0.3 dB) because the amount of electrical field summation for adjacent electrodes is relatively high.

Figure 9A:
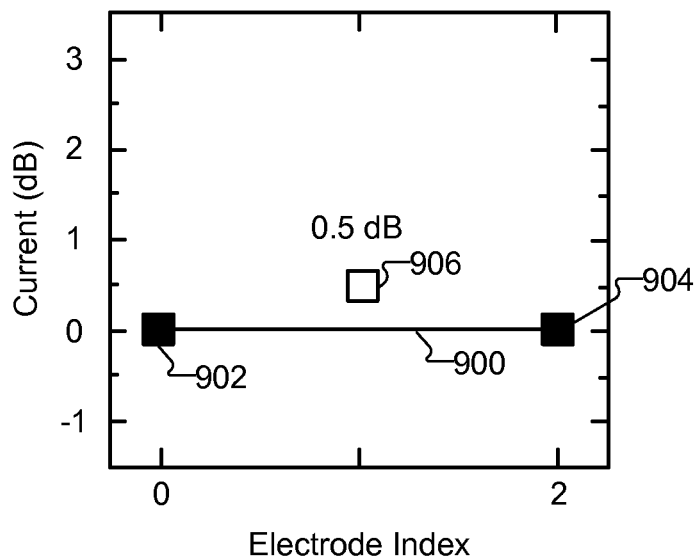
FIG. 9A-9C show a number of equal loudness contours for various non-adjacent electrode configurations according to principles described herein.
Figure 9B:
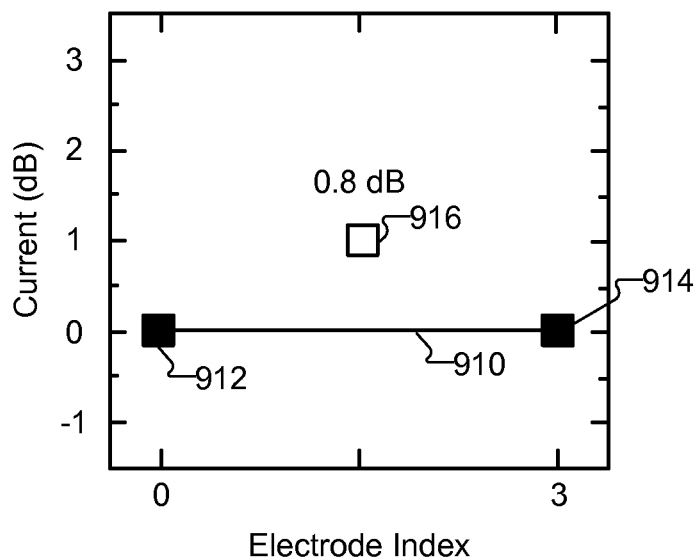
Figure 9C:
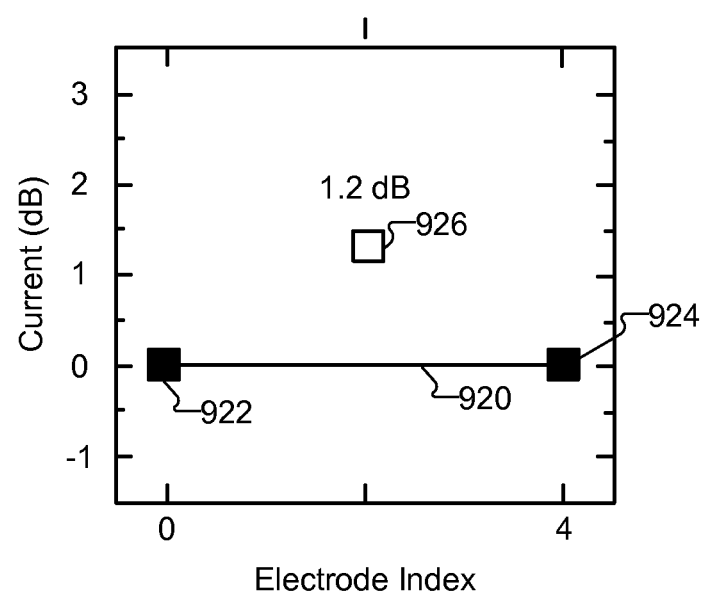

FIGS. 9A-9C show a number of equal loudness contours for various non-adjacent electrode configurations. As shown in FIGS. 9A-9C, the stimulation current is measured in a decibel (dB) scale to facilitate comparison with other equal loudness contours.

FIG. 9A illustrates an exemplary loudness contour 900 corresponding to a non-adjacent electrode configuration wherein stimulation current is simultaneously applied to two non-adjacent electrodes (e.g., electrodes 114-1 and 114-3). These electrodes 114-1 and 114-3 may be separated by any separation distance (e.g., 2 mm) as may serve a particular application.

As shown in FIG. 9A, most comfortable current levels corresponding to each electrode 114-1 and 114-3 are represented by data points 902 and 904, respectively. The most comfortable current level corresponding to dual stimulation of both electrodes 114-1 and 114-3 is represented by data point 906.

The most comfortable current level 906 has an elevation of 0.5 dB, which is greater than the most comfortable current level 806 shown in FIGS. 8A and 8B. In other words, more current is required for dual electrode stimulation than single electrode stimulation to achieve the same loudness level. This is because the distance between non-adjacent electrodes 114-1 and 114-3 is greater than the distance between adjacent electrodes 114-1 and 114-2.

FIG. 9B illustrates an exemplary loudness contour 910 corresponding to a non-adjacent electrode configuration wherein stimulation current is simultaneously applied to two non-adjacent electrodes (e.g., electrodes 114-1 and 114-4) separated by a separation distance that is greater than that of the electrode configuration shown in FIG. 9A. For example, electrodes 114-1 and 114-4 may be separated by 3 mm or any other suitable separation distance.

As shown in FIG. 9B, most comfortable current levels corresponding to each electrode 114-1 and 114-4 are represented by data points 912 and 914, respectively. The most comfortable current level corresponding to dual stimulation of both electrodes 114-1 and 114-4 is represented by data point 916.

The most comfortable current level 916 has an elevation of 0.8 dB, which is greater than the most comfortable current levels 806 and 906 because of the relatively greater distance separating electrodes 114-1 and 114-4.

FIG. 9C illustrates an exemplary loudness contour 920 corresponding to a non-adjacent electrode configuration wherein stimulation current is simultaneously applied to two non-adjacent electrodes (e.g., electrodes 114-1 and 114-5) separated by a separation distance that is greater than that of the electrode configuration shown in FIG. 9B. For example, electrodes 114-1 and 114-5 may be separated by 4 mm or any other suitable separation distance.

As shown in FIG. 9C, most comfortable current levels corresponding to each electrode 114-1 and 114-5 are represented by data points 922 and 924, respectively. The most comfortable current level corresponding to dual stimulation of both electrodes 114-1 and 114-5 is represented by data point 926.

The most comfortable current level 926 has an elevation of 1.2 dB, which is greater than the most comfortable current levels 806, 906, and 916 because of the relatively greater distance separating electrodes 114-1 and 114-5.

As shown in FIGS. 9A-9C, the amount of elevation is inversely proportional to the degree of electrical field summation. Hence, there is a slight increase in the amount of elevation as a function of electrode spacing. To compensate for this increase in elevation, the amount of stimulation current applied to the non-adjacent electrodes may be increased. However, the amount of elevation is less than 1 dB for electrode spacing of up to 3 mm and in some patients up to 4 mm. This shows that there is summation of electrical fields between non-adjacent electrodes separated by distances of up to and including 4 mm. Therefore, in this particular example, implantable cochlear stimulator 110 may be configured to simultaneously apply stimulation current to at least two non-adjacent electrodes separated one from another up to 4 mm in order to generate a pitch associated with a disabled electrode disposed in between the non-adjacent electrodes. It will be recognized that the non-adjacent electrodes may be separated by any distance as may serve a particular application and that distances of up to 4 mm are merely given for illustrated purposes.

In some examples, one or more equal loudness contours may be generated in order to determine a maximum separation distance that may be present between non-adjacent electrodes in order for the non-adjacent electrodes to effectively generate a pitch associated with a disabled electrode. For example, equal loudness contours may be generated for each of a plurality of electrode combinations having different separation distances. A maximum separation distance may be determined by determining a separation distance that results in an elevation that is above a predefined threshold. Any electrode associated with a separation distance that results in an elevation that is below the predefined threshold may be effectively used in simultaneous dual electrode stimulation to generate a pitch associated with a disabled electrode.

To illustrate the effectiveness of current steering between non-adjacent electrodes in generating pitches associated with disabled electrodes, a study was performed wherein stimulation was applied via six different electrode configurations or maps to nine cochlear implant patients. Test sentences were used to measure sentence recognition scores for the six electrode maps. Sentence tokens were presented at 65 dB SPL and speech recognition scores were measured in "quiet" and in the presence of background "noise" (i.e., 4-talker babble with 10 dB signal-to-noise ratio).

FIG. 10 shows the six electrode maps 1000 that were used in the study. As shown in FIG. 10, each electrode map included a different combination of enabled electrodes out of 16 available electrodes. Table 1 is a summary of the electrode maps in FIG. 10.

TABLE 1

| Map | Electrode Map | Disabled Electrodes | Virtual Electrodes |
|---|---|---|---|
| 1 | 16 electrode baseline | none | none |
| 2 | 9 electrode SPAN | 2, 4, 6, 8, 10, 12, 14 | 7 electrodes |
| 3 | 13 electrode SPAN | 3, 4, 5 | 3 electrodes |
| 4 | 13 electrode SPAN | 12, 13, 14 | 3 electrodes |
| 5 | 13 electrode GAP | 3, 4, 5 | — |
| 6 | 13 electrode GAP | 12, 13, 14 | — |

As used herein, "SPAN" refers to simultaneous non-adjacent dual electrode stimulation and "GAP" refers to a configuration wherein the frequency region corresponding to the disabled electrodes is redistributed to the active electrodes. In other words, current steering is not used in GAP configurations.

As shown in FIG. 10 and in Table 1, various electrodes were disabled in each electrode map other than the baseline map. For example, three adjacent electrodes (electrodes 3, 4, and 5) in the third map were disabled. In this example, simultaneous stimulation was applied to the second and sixth electrodes to create virtual electrodes representing the disabled electrodes.

As mentioned, simultaneous stimulation of non-adjacent electrodes is advantageous over sequential stimulation of non-adjacent electrodes because simultaneous stimulation requires less stimulation current to effectively generate a pitch associated with a disabled electrode surrounded by the electrodes. For example, if simultaneous stimulation of non-adjacent electrodes (e.g., electrodes 114-1 and 114-3) is used to generate a pitch equivalent to a current ratio between the non-adjacent electrodes of 30/70, 50/50 and 70/30, the current level needed would be roughly the same for each current ratio (e.g., 400 microamps). However, to generate the same pitch using sequential stimulation of the non-adjacent electrodes, the current level needed would vary per current ratio (e.g., 450, 750, and 500 microamps). Hence, balancing loudness levels to generate a desired pitch using sequential stimulation of non-adjacent electrodes may be difficult, less effective, and inefficient.

Figure 11:
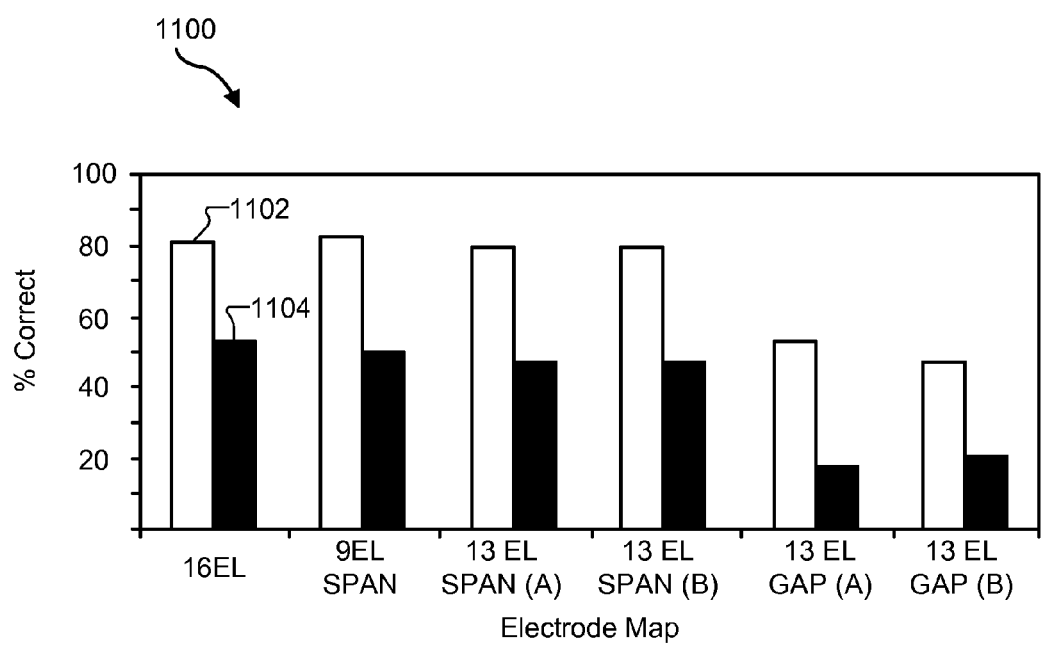
FIG. 11 shows a graph illustrating average speech recognition scores for a group of cochlear implant patients according to principles described herein.

FIG. 11 is a graph 1100 illustrating the average speech recognition scores for the six electrode maps across nine cochlear implant patients. Non-shaded bars (e.g., bar 1102) represent average speech recognition scores obtained in a quiet environment. Shaded bars (e.g., bar 1104) represent average speech recognition scores obtained in a noisy environment. As shown in FIG. 11, the average speech recognition scores for each of the SPAN configurations were relatively close to those of the baseline configuration having no disabled electrodes. However, the average speech recognition scores for the GAP configurations were significantly lower than the scores of the baseline configuration.

Hence, the study showed that simultaneous stimulation of non-adjacent electrodes surrounding at least one disabled electrode is an effective method of compensating for the loss of stimulation resulting from the at least one disabled electrode. In other words, pitches associated with the disabled electrodes were effectively generated by the simultaneous stimulation of the non-adjacent electrodes.

Figure 12:
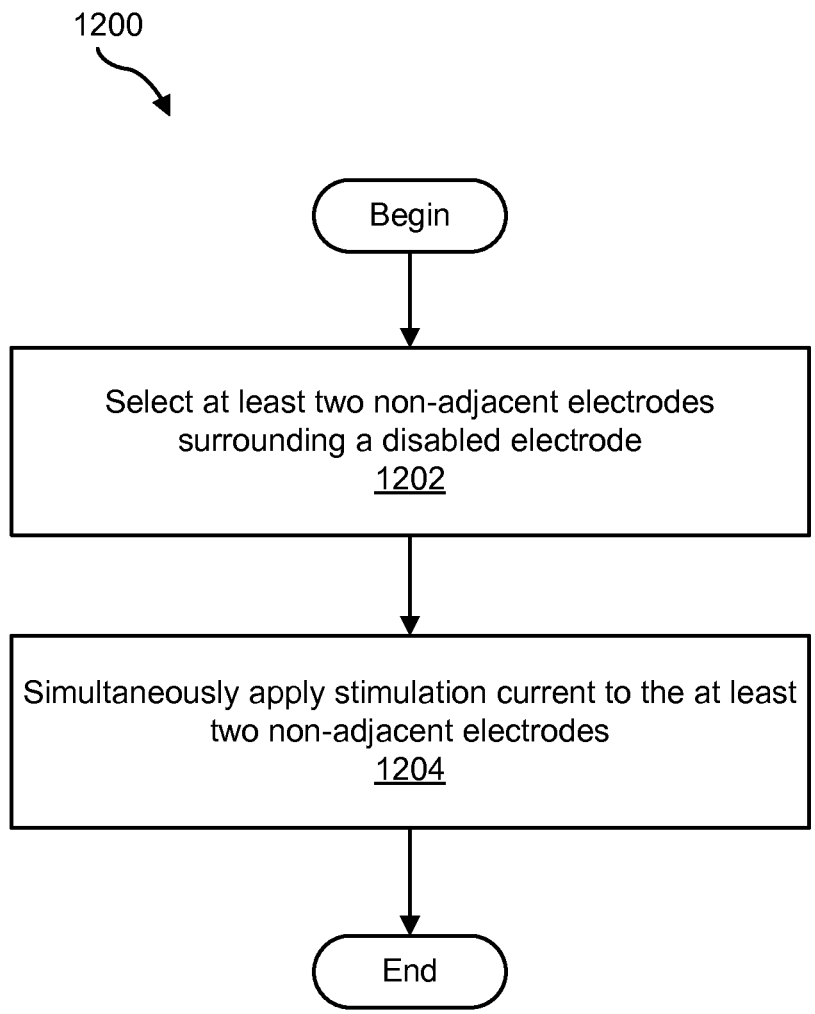
FIG. 12 illustrates an exemplary method of compensating for a disabled electrode according to principles described herein.

FIG. 12 illustrates an exemplary method of compensating for a disabled electrode within an array of electrodes. While FIG. 12 illustrates exemplary steps according to one embodiment, other embodiments may omit, add to, reorder, and/or modify any of the steps shown in FIG. 12.

In step 1202, at least two non-adjacent electrodes within the array of electrodes and surrounding the disabled electrode are selected. For example, the sound processing unit 106, implantable cochlear stimulator 110, and/or any other component may be configured to select the at least two non-adjacent electrodes. In some examples, the non-adjacent electrodes may be selected based on a separation distance that separates them one from another. For example, non-adjacent electrodes having a separation distance below a predetermined threshold or within a range that yields satisfactory stimulation results at a stimulation site associated with the disabled electrode may be selected.

In step 1204, stimulation current is simultaneously applied to the at least two non-adjacent electrodes. The stimulation current may be configured to generate a pitch associated with the disabled electrode. The application of stimulation current may be performed in accordance with a current steering heuristic, for example, and may be performed by implantable cochlear stimulator 110. In some examples, sound processing unit 106 may be configured to direct implantable cochlear stimulator 110 to apply the stimulation current in accordance with one or more stimulation parameters. The stimulation parameters may define the amount of stimulation current applied to each non-adjacent electrode, for example.

Figure 13:
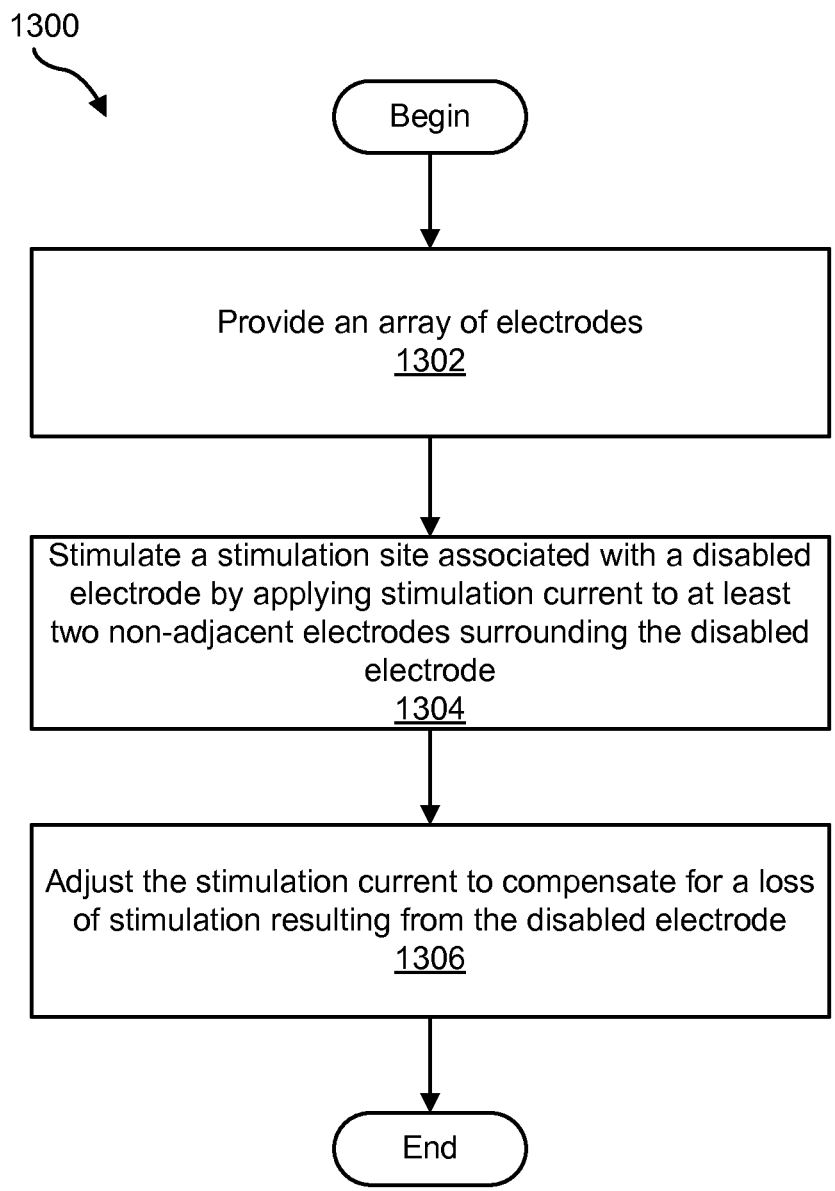
FIG. 13 illustrates another exemplary method of compensating for a disabled electrode according to principles described herein.

FIG. 13 illustrates another exemplary method of compensating for a disabled electrode within an array of electrodes. While FIG. 13 illustrates exemplary steps according to one embodiment, other embodiments may omit, add to, reorder, and/or modify any of the steps shown in FIG. 13. Any of the steps shown in FIG. 13 may be performed by sound processing unit 106, implantable cochlear stimulator 110, and/or any other component.

In step 1302, an array of electrodes may be provided. The array of electrodes may be disposed on a lead configured to be inserted into a duct of a cochlea of a patient, for example.

In step 1304, a stimulation site associated with a disabled electrode may be stimulated by applying stimulation current to at least two non-adjacent electrodes surrounding the disabled electrode. The stimulation current may be applied in any of the ways described herein.

In step 1306, the stimulation current is adjusted to compensate for a loss of stimulation resulting from the disabled electrode. The stimulation current may be adjusted in any of the ways described herein. For example, specific amounts of the stimulation current applied to each non-adjacent electrode may be adjusted in accordance with one or more stimulation parameters provided by sound processing device 106. In some examples, the stimulation current is configured to compensate for a loss of stimulation resulting from the disabled electrode by generating a pitch associated with the disabled electrode.

In some examples, the systems and methods described herein may be configured to compensate for the loss of stimulation that results from multiple disabled electrodes. This is advantageous in situations where a patient would otherwise have to have the electrode lead explanted and replaced with a new lead.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
   identifying, by a cochlear implant system, an electrode included within an array of electrodes as being a disabled electrode;
   selecting, by the cochlear implant system, at least two non-adjacent electrodes surrounding the disabled electrode; and
   generating, by the cochlear implant system, a pitch associated with the disabled electrode by simultaneously applying stimulation current to the at least two non-adjacent electrodes.

2. The method of claim 1, wherein the stimulation current is configured to generate the pitch by providing an electric field at a stimulation site associated with the disabled electrode.

3. The method of claim 1, wherein the array of electrodes is disposed on a lead configured to be inserted within a duct of cochlea of a patient.

4. The method of claim 1, further comprising generating the stimulation current with an implantable cochlear stimulator.

5. The method of claim 1, wherein the simultaneously applying the stimulation current to the at least two non-adjacent electrodes comprises:
   applying a first weighted portion of the stimulation current to one of the at least two non-adjacent electrodes; and
   applying a second weighted portion of the stimulation current to another of the at least two non-adjacent electrodes.

6. The method of claim 1, wherein the at least two non-adjacent electrodes are within a predefined separation distance of each other.

7. The method of claim 6, wherein the predefined separation distance is substantially equal to or less than four millimeters.

8. The method of claim 6, further comprising determining the predefined separation distance using one or more equal loudness contours.

9. The method of claim 1, wherein the at least two non-adjacent electrodes further surround at least one additional disabled electrode, and wherein the stimulation current is further configured to compensate for a loss of stimulation resulting from the at least one additional disabled electrode.

10. A method comprising:
    identifying, by a sound processor, an electrode included within an array of electrodes as being a disabled electrode;
    selecting, by the sound processor, at least two non-adjacent electrodes surrounding the disabled electrode; and
    directing, by the sound processor, an implantable cochlear stimulator to generate a pitch associated with the disabled electrode by simultaneously applying stimulation current to the at least two non-adjacent electrodes to compensate for a loss of stimulation resulting from the disabled electrode.

11. The method of claim 10, wherein the directing comprises:
    directing the implantable cochlear stimulator to apply a first weighted portion of the stimulation current to one of the at least two non-adjacent electrodes; and
    directing the implantable cochlear stimulator to apply a second weighted portion of the stimulation current to another of the at least two non-adjacent electrodes.

12. The method of claim 10, wherein the at least two non-adjacent electrodes are within a predefined separation distance of each other.

13. The method of claim 12, wherein the predefined separation distance is substantially equal to or less than four millimeters.

14. The method of claim 12, further comprising determining, by the sound processor, the predefined separation distance using one or more equal loudness contours.

15. A system comprising:
    an implantable cochlear stimulator; and
    a sound processor communicatively coupled to the implantable cochlear stimulator, wherein the sound processor
       identifies an electrode included within an array of electrodes as being a disabled electrode,
       selects at least two non-adjacent electrodes surrounding the disabled electrode, and directs the implantable cochlear stimulator to generate a pitch associated with the disabled electrode by simultaneously applying stimulation current to the at least two non-adjacent electrodes to compensate for a loss of stimulation resulting from the disabled electrode.

16. The system of claim 15, wherein the stimulation current is configured to compensate for the loss of the stimulation resulting from the disabled electrode by generating a pitch associated with the disabled electrode.

17. The system of claim 15, wherein the sound processor directs the implantable cochlear stimulator to simultaneously apply the stimulation current to the at least two non-adjacent electrodes by:
  directing the implantable cochlear stimulator to apply a first weighted portion of the stimulation current to one of the at least two non-adjacent electrodes; and
  directing the implantable cochlear stimulator to apply a second weighted portion of the stimulation current to another of the at least two non-adjacent electrodes.

18. The system of claim 15, wherein the at least two non-adjacent electrodes are within a predefined separation distance of each other.

\* \* \* \* \*